United States Patent [19]

Wu

[11] Patent Number: 5,315,026

[45] Date of Patent: May 24, 1994

[54] PROCESS FOR PREPARING ARYL-SUBSTITUTED ALIPHATIC CARBOXYLIC ACIDS AND THEIR ESTERS USING CYCLIC PHOSPHINE CATALYSTS

[75] Inventor: Tse-Chong Wu, Baton Rouge, La.

[73] Assignee: Ethyl Corporation, Richmond, Va.

[21] Appl. No.: 128,405

[22] Filed: Sep. 29, 1993

[51] Int. Cl.$^5$ .............................................. C07C 69/76
[52] U.S. Cl. .................................. 560/105; 562/406; 560/100; 560/20; 560/21; 560/55; 560/56
[58] Field of Search ....................... 560/105, 9, 20, 21, 560/55, 56, 100; 562/406

[56] References Cited

U.S. PATENT DOCUMENTS

| | | | |
|---|---|---|---|
| 4,656,306 | 4/1987 | Takaki | 560/104 |
| 4,694,100 | 9/1987 | Shimizu | 560/105 |
| 4,739,110 | 4/1988 | Drent | 560/207 |
| 4,786,443 | 11/1988 | Drent | 260/549 |
| 4,937,362 | 6/1990 | Tanaka | 562/406 |
| 5,028,734 | 7/1991 | Drent | 562/406 |
| 5,179,224 | 1/1993 | Takaki | 560/105 |
| 5,254,720 | 10/1993 | Wu | 560/105 |

*Primary Examiner*—Paul J. Killos

*Attorney, Agent, or Firm*—Richard J. Hammond

[57] ABSTRACT

A catalytic process for preparing aryl substituted aliphatic carboxylic acid esters is disclosed. A 1-aryl substituted olefinic compound is reacted with carbon monoxide in the presence of an alcohol in anhydrous conditions at a temperature between about 25° C. and about 200° C. An excess of several moles of anhydrous alcohol is preferred. An acid such as hydrochloric acid may also be added. As catalyst, a mixture of a palladium compound and a copper compound is used with at least one acid-stable cyclic phosphine having the formula:

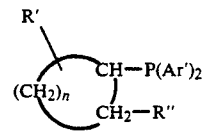

where R' is the same or different than R" and is alkyl or aryl, said aryl, either substituted or unsubstituted, and Ar' is phenyl, naphthyl, substituted phenyl or substituted naphthyl and n is an integer from 3 to 6.

28 Claims, No Drawings

PROCESS FOR PREPARING ARYL-SUBSTITUTED ALIPHATIC CARBOXYLIC ACIDS AND THEIR ESTERS USING CYCLIC PHOSPHINE CATALYSTS

TECHNICAL FIELD

This invention relates to a process for preparing aryl-substituted aliphatic carboxylic acids and esters.

BACKGROUND OF THE INVENTION

Among the processes known for preparing 2-(4-isobutylphenyl)propionic acid or esters thereof is that of Shimizu et al. (U.S. Pat. No. 4,694,100, issued September, 1987), who teach the reaction of p-isobutylstyrene with carbon monoxide and water or alcohol in the presence of a palladium catalyst and a mineral acid, e.g., HCl. This patent also teaches the alternative reaction of p-isobutylstyrene with carbon monoxide and hydrogen in the presence of a metal complex carbonyl catalyst to produce 2-(4-isobutylphenyl)propionaldehyde, which is then oxidized to produce the desired product. The preparation of the starting material for this reaction is disclosed as the reaction of isobutylbenzene with acetaldehyde in the presence of sulfuric acid, producing 1,1-bis(4-isobutylphenyl)ethane, which is then catalytically cracked to produce p-isobutylstyrene and isobutylbenzene.

Another process for preparing ibuprofen is that of European Patent Application 284,310 (Hoechst Celanese, published September, 1988), which teaches that ibuprofen can be prepared by carboxylating 1-(4-isobutylphenyl)ethanol with carbon monoxide in an acidic aqueous medium and in the presence of a palladium compound/phosphine comple and dissociated hydrogen and halide ions, which are preferably derived from a hydrogen halide. This process has the disadvantage of starting with 1-(4-isobutylphenyl)ethanol, a compound which is not economical to make by known processes.

Gardano et al. (U.S. Pat. No. 4,536,595, issued August, 1985) teach the preparation of alkaline salts of certain alphaarylpropionic acids by reaction with carbon monoxide, at substantially ambient temperature and pressure conditions, of the corresponding arylethyl secondary halide in an anhydrous alcoholic solvent in the presence of alkaline hydroxides and, as catalyst, a salt of cobalt hydrocarbonyl.

Alper et al. in *J. Chem. Soc. Chem. Comm.*, 1983, 1270-1271, discloses that alkenes can react with carbon monoxide, water, hydrochloric acid and a mixture of palladium and copper to produce the hydrocarboxylated product, branched chain carboxylic acid. Oxygen is necessary to succeed in the reaction. Subsequently, Alper et al. have disclosed similar catalyst systems, but employing a chiral ligand, as being successful in asymmetric hydrocarboxylation reactions. See Alper et al., PCT Application, WO 91 03,452 and *J. Am. Chem. Soc.*, 112, 2803-2804 (1990).

Another process for preparing ibuprofen is that of Japanese Patent Application (Kokai) No. 59-10,545 (Mitsubishi Petrochemical, published January, 1984), which teaches that ibuprofen can be prepared by reacting p-isobutylstyrene with carbon monoxide and water or alcohol in the presence of a palladium (II) catalyst and a peroxide, e.g., cumyl hydroperoxide.

THE INVENTION

In the following specification, the meaning of the substituent groups is as follows: "alkyl" means straight or branched chain alkyl having 1 to 20 carbon atoms and includes, for example, methyl, ethyl, propyl, isopropyl, butyl, isobutyl, secondary butyl, tertiary butyl, pentyl, isopentyl, neopentyl, hexyl, heptyl, octyl, 2-ethylhexyl, 1,1,3,3-tetramethylbutyl, nonyl, decyl, dodecyl, tetradecyl, hexadecyl, octadecyl and eicosyl, and the like (for the purposes of this definition, "alkyl".is also "aliphatic" and also includes "$C_1$ to $C_6$ alkyl" which is 1 to 6 linear or branched carbon atoms);

"cycloalkyl" means cyclic alkyl having 3 to 7 carbon atoms and includes cyclopropyl, cyclobutyl, cyclopentyl, cyclohexyl, cycloheptyl and the like;

"substituted aryl" means phenyl or naphthyl substituted by at least one substituent selected from the group consisting of halogen (chlorine, bromine, fluorine or iodine), amino, nitro, hydroxy, alkyl, alkoxy which means straight or branched chain alkoxy having 1 to 10 carbon atoms, and includes, for example, methoxy, ethoxy, propoxy, isopropoxy, butoxy, isobutoxy, secondary butoxy, tertiary butoxy, pentyloxy, isopentyloxy, hexyloxy, heptyloxy, octyloxy, nonyloxy and decyloxy, aryloxy including phenoxy and phenoxy substituted with halo, alkyl, alkoxy and the like, haloalkyl which means straight or branched chain alkyl having 1 to 8 carbon atoms which is substituted by at least one halogen, and includes, for example, chloromethyl, bromomethyl, fluoromethyl, iodomethyl, 2-chloroethyl, 2-bromoethyl, 2-fluoroethyl, 3-chloropropyl, 3-bromopropyl, 3-fluoropropyl, 4-chlorobutyl, 4-fluorobutyl, dichloromethyl, dibromomethyl, difluoromethyl, diiodomethyl, 2,2-dichloroethyl, 2,2-diibromoethyl, 2,2-difluoroethyl, 3,3-dichloropropyl, 3,3-difluoropropyl, 4,4-dichlorobutyl, 4,4-difluorobutyl, trichloromethyl, trifluoromethyl, 2,2,2-trifluoroethyl, 2,3,3-trifluoropropyl, 1,1,2,2-tetrafluoroethyl, 2,2,3,3-tetrafluoropropyl and the like;

"alkyl-substituted cycloalkyl" means that the cycloalkyl moiety is cyclic alkyl having 3 to 7 carbon atoms and the alkyl moiety is straight or branched chain alkyl having 1 to 8 carbon atoms, and includes, for example, cyclopropylmethyl, cyclobutylmethyl, cyclopentylmethyl, cyclohexylmethyl, cycloheptylmethyl, 2-cyclopropylethyl, 2-cyclopentylethyl, 2-cyclohexylethyl, 3-cyclopropylpropyl, 3-cyclopentylpropyl, 3-cyclohexylpropyl, 4-cyclopropylbutyl, 4-cyclopentylbutyl, 4-cyclohexylbutyl, 6-cyclopropylhexyl, 6-cyclohexylhexyl and the like;

"alkylthio" means a divalent sulfur with alkyl occupying one of the valencies and includes the groups methylthio, ethylthio, propylthio, butylthio, pentylthio, hexylthio, octylthio and the like;

"heteroaryl" means 5 to 10 membered mono- or fused-heteroaromatic ring which has at least one heteroatom and includes those selected from the group consisting of nitrogen, oxygen and sulfur, and includes, for example, 2-furyl, 3-furyl, 2-thienyl, 3-thienyl, 2-pyridyl, 3-pyridyl, 4-pyridyl, pyrazolyl; imidazolyl, pyrimidinyl, pyridazinyl, pyrazinyl, benzimidazolyl, quinolyl, oxazolyl, thiazolyl, indolyl and the like;

"substituted heteroaryl" means 5 to 10 membered mono- or fused-heteroaromatic ring which has at least one heteroaromatic selected from the group consisting of nitrogen, oxygen and sulfur and which is substituted by at least one substituent selected from the group consisting of halogen, amino, nitro, hydroxy, alkyl, alkoxy and haloalkyl on the above-mentioned heteroaromatic nucleus;

"alkanoyl" means alkanoyl having 2 to 18 carbon atoms and includes, for example, acetyl, propionyl, butyryl, isobutyryl, pivaloyl, valeryl, hexanoyl, octanoyl, lauroyl, stearoyl and the like;

"aroyl" means benzoyl or naphthoyl;

"substituted aroyl" means benzoyl or naphthoyl substituted by at least one substituent such including those selected from the group consisting of halogen, amino, nitro, hydroxy, alkyl, alkoxy and haloalkyl on the benzene or naphthalene ring;

"heteroarylcarbonyl" means that the heteroaryl moiety is 5 to 10 membered mono- or fused-heteroaromatic ring having at least one heteroatom selected from the group consisting of nitrogen, oxygen and sulfur as mentioned above, and includes, for example, furoyl, thinoyl, nicotinoyl, isonicotinoyl, pyrazolylcarbonyl, imidazolylcarbonyl, pyrimidinylcarbonyl, benzimidazolylcarbonyl and the like;

"substituted heteroarylcarbonyl" means the above-mentioned heteroarylcarbonyl which is substituted by at least one substituent selected from the group consisting of halogen, amino, nitro, hydroxy, alkoxy and haloalkyl on the heteroaryl nucleus; and includes, for example, 2-oxo-1,3-dioxolan-4-ylmethyl, 2-oxo-1,3-dioxan-5-yl and the like.

The present invention embraces any salts, racemates and individual optical isomers thereof of the compounds of the following formula (I) having a chiral carbon atom.

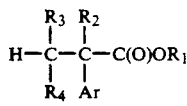

where $R_1$, $R_2$, $R_3$ and $R_4$ are the same or different and are hydrogen, alkyl, cycloalkyl, alkyl-substituted cycloalkyl, aryl either substituted or unsubstituted, alkoxy, alkylthio, heteroaryl either substituted or unsubstituted, alkanoyl, aroyl either substituted or unsubstituted, heteroarylcarbonyl either substituted or unsubstituted, trifluoromethyl or halo and Ar is unsubstituted or substituted aryl.

In accordance with the present invention, aryl-substituted aliphatic carboxylic acid esters are prepared by carboxylating an aryl-substituted, olefinic compound with carbon monoxide in a neutral or acidic medium containing at least 1 mol of water or a $C_1$ to about $C_8$ linear or branched aliphatic alcohol per mol of olefinic compound at a temperature of between about 25° C. and about 200° C. and a carbon monoxide pressure of at least about one atmosphere in the presence of (a) palladium metal or a palladium compound in which the palladium has a valence of 1 or 2 or (b) a mixture of (i) such palladium metal or palladium compound and (ii) a copper compound having a valence of 1 or 2 and (c) a ligand of the formula:

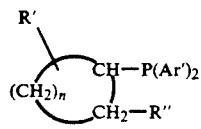

where R' is the same or different than R" and is alkyl or aryl either substituted or unsubstituted and Ar' is phenyl, naphthyl, substituted phenyl or substituted naphthyl and n is an integer from 3 to 6.

In place of the aliphatic alcohol, an alcohol equivalent can be used. These include the trialkyl orthoalkonates, dialkyl ketals, alkyl formates, trialkyl borates, or titanium alkoxides. These materials provide a "source of alkoxide ions" as further defined herein. The esters may be readily converted to the corresponding free carboxylic acids or salts by well known conventional methods.

The olefinic-containing compound which is catalytically carboxylated in the practice of this invention has the formula:

where, Ar is unsubstituted or substituted aryl and $R_2$, $R_3$ and $R_4$ are hydrogen, alkyl, cycloalkyl, substituted or unsubstituted aryl, alkoxy, alkylthio, substituted or unsubstituted heteroaryl alkanoyl, substituted or unsubstituted aroyl, substituted or unsubstituted heteroarylcarbonyl, trifluoromethyl or halo.

Preferably, in the compounds of formula II, Ar is unsubstituted or substituted aryl, $R_2$, $R_3$ and $R_4$ are hydrogen, $C_1$ to $C_2$ alkyl, substituted or unsubstituted phenyl or trifluoromethyl.

Most preferably Ar is phenyl substituted with alkyl or naphthyl substituted with alkoxy, $R_2$, $R_3$ and $R_4$ are hydrogen, methyl or trifluoromethyl.

The catalytic carboxylation of the compound of formula II is conducted, at a temperature between about 25° C. and about 200° C., preferably about 25°–120° C., and most preferably about 25°–100° C. Higher temperatures can also be used. It has been found that a small advantage in yield is obtained by gradually increasing the temperature within the preferred ranges during the course of the reaction.

The partial pressure of carbon monoxide in the reaction vessel is at least about 1 atmosphere (14.7 psig) at ambient temperature (or the temperature at which the vessel is charged). Any higher pressures of carbon monoxide can be used up to the pressure limits of the reaction apparatus. A pressure up to about 3000 psig is convenient in the process. More preferred is a pressure from 0 to about 3000 psig at the reaction temperature and most preferred is a pressure from 0 to about 1,000 psig. It should be noted that the presence of oxygen is undesirable in the hydrocarboxylation reaction of this invention. Hence, an atmosphere of 100% carbon monoxide is most preferred to carry out this process. Various inert gases can, however, be incorporated in the reaction mass (nitrogen, argon, etc.) the only criteria being that the process should not be slowed to the point of requiring exceptionally long periods to complete the reaction.

The carboxylation is conducted in the presence of at least about one mol of water or aliphatic alcohol per mol of the compound of formula II; however, an excess is preferred in order to assist in driving the reaction to completion. Although there is no real upper limit to the amount of water or alcohol except that imposed by practicality (e.g. the size of the reaction vessel), an amount up to about 100 mols per mol of the compounds of formula II is useful in the process. Further, controlling the amount of water or alcohol used in the process of this invention is advantageous in terms of producing the highest yields. Therefore, an amount from about 1 to about 50 mols of water or alcohol per mol of the compounds of formula II is preferred, and an amount from about 2 to about 24 mols of water or alcohol per mol of the such olefinic compound is most preferred. The product of the reaction is a carboxylic acid (where $R_1$ is hydrogen) or carboxylic acid ester (where $R_1$ is alkyl). These compounds have the following formula:

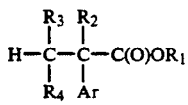

where $R_1$ is hydrogen or alkyl and Ar, $R_2$, $R_3$ and $R_4$ are as previously defined.

Any alcohol which produces an ester of the carboxylic acid may be used in the practice of this invention. In a preferred embodiment, the lower aliphatic alcohols, are used. Examples of the alcohols to be used in this embodiment include methyl alcohol, ethyl alcohol, n-propyl alcohol, isopropyl alcohol, n-, iso- sec-, and tert-butyl alcohols, the pentyl alcohols, the hexyl alcohols, etc. Methyl alcohol is highly preferred, and ethyl alcohol is most highly preferred. Other alcohols, glycols, or aromatic hydroxy compounds may also be used. In the broadest sense, these alcohols provide a source of alkoxide ions for this reaction. However, any other "source of alkoxide ions" may also be used. The source of such alkoxide ions is from a compound selected from the group consisting of $HC(OR_1)_3$, $(R)_2C(OR_1)_2$, $HC(O)OR_1$, $B(OR_1)_3$, $Ti(OR_1)_4$ and $Al(OR_1)_3$ where R is hydrogen or individually the same or different than $R_1$ and $R_1$ is as previously defined.

In a preferred embodiment of this invention, the carboxylation reaction is initiated under neutral conditions, i.e., with no added acid. It can also be performed in the presence of an added acid. When acids are added, such acids include sulfuric acid, phosphoric acid or sulfonic acids. A hydrogen halide acid such as hydrochloric or hydrobromic acid is preferred. The hydrogen halide may be added as a gas phase or as a liquid phase. Any concentration may be used. Hydrochloric acid is particularly preferred, at a concentration up to about 10%; more highly preferred is a concentration from about 10% to about 30%. The amount of acid added is such as to provide up to about 40 mols of hydrogen ion per mol of compound of formula II; more preferred is an amount to provide up to about 10 mols of hydrogen ion per mol of compound; the most preferred amount provides up to about 4 mols of hydrogen ion per mol of the compounds of formula II.

The catalytic carboxylation process of this invention is conducted in the presence of a reaction-promoting quantity of i) palladium metal or a palladium compound in which the palladium has a valence of 1 or 2 or ii) a mixture of a palladium metal or palladium compound and a copper compound, with iii) a cyclic ligand. The compounds of palladium and copper are sometimes referred to as palladium and copper salts. Cyclic ligands which may be used have the formula:

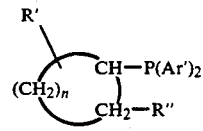

where R' is the same or different than R" and are individually alkyl, aryl or substituted aryl, Ar is phenyl, naphthyl, substituted phenyl or substituted naphthyl and n is an integer from 3 to 6. Preferably, R' and R" are the same or different and are $C_1$ to $C_6$ alkyl, Ar' is phenyl or naphthyl and n is 3 or 4. Most preferably, R' is methyl or ethyl, R" is $C_1$ to $C_6$ branched alkyl, Ar' is phenyl and n is 4. Especially preferred is neomenthyldiphenylphosphine as a ligand.

In one embodiment, palladium and copper compounds are inorganic salts and are added as a preformed complex of, for example, palladium(II) chloride or bromide, copper(II) chloride or bromide and carbon monoxide or any other similar complex. In a preferred embodiment, active catalytic species are formed in situ by the addition to the reaction mixture of the individual components, i.e., a ligand, a copper compound, and a palladium compound such as the inorganic salts of palladium(II) and copper(II). These inorganic salts include the chlorides, bromides, nitrates, sulfates, or acetates. In the most preferred embodiment, neomenthyldiphenylphosphine, copper(II) chloride, and palladium(II) chloride are used and are added individually or together, either simultaneously or sequentially.

The palladium metal or the palladium compound or the mixture of palladium and copper compounds can be supported on carbon, silica, alumina, zeolite, clay and other polymeric materials and used as the heterogeneous catalysts.

The amount of the mixture of copper and palladium compounds or of palladium metals or its compounds preferably employed is such as to provide from about 4 to about 8000 mols of the compound of formula II per mol of the mixture of metal salts or of metal or metal salt; more preferred is an amount to provide from about 10 to about 4000 mols of compound of formula II per mol of the mixture; the most preferred amounts provide from about 20 to 2000 mols of the compounds of formula II per mol of the metal salt mixture. The process of this invention is conducted in the presence of at least one mol of the cyclic ligand per mol of the mixture of the metal and salt or metal salts. More preferably, about 1 to about 40 mols of ligand per mol of the mixture are present, and most preferably about 1 to about 20 mols of ligand per mol of the mixture are used.

The presence of a solvent is not required in the process of this invention, although it may be desirable in some circumstances. Those solvents which can be used include one or more of the following: ketones, for example, acetone, methyl ethyl ketone, diethyl ketone, methyl-n-propyl ketone, acetophenone, and the like; linear, poly and cyclic ethers, for example, diethyl ether, di-n-propyl ether, di-n-butyl ether, ethyl-n-propyl ether, glyme (the dimethyl ether of ethylene glycol), diglyme (the dimethyl ether of diethylene glycol), tetrahydrofuran, dioxane, 1,3-dioxolane, and similar compounds; and aromatic hydrocarbons, for example, toluene, ethyl benzene, xylenes, and similar compounds. Alcohols are also suitable as solvents, for example, methanol, ethanol, 1-propanol, 2-propanol isomers of butanol, isomers of pentanol, etc. Acids and esters may also be used, such as formic or acetic acid or ethyl acetate etc. When an ester or an alcohol is used as solvent, the product is the corresponding ester of the carboxylic acid. Most highly preferred are ethers, especially tetrahydrofuran. When solvents are used, the amount can be up to about 100 mL per gram of the compounds of formula II, but the process is most advantageously conducted in the presence of about 1 to 30 mL per gram of the compound of formula II.

In those specific embodiments of this invention in which an acid or an ester of ibuprofen is produced, the ester may be conveniently converted to the acid (ibuprofen itself) by conventional methods of hydrolysis.

The following examples are given to illustrate the process of this invention and are not intended as a limitation thereof.

EXAMPLES

EXAMPLE 1

$PdCl_2$ (29 mg, 0.16 mmol), $CuCl_2$ (50 mg, 0.37 mmol), and (+)-neomenthyldiphenylphosphine (NMDP) (0.16 g, 0.49 mmol) were stirred in THF (degassed, 30 mL) in a round-bottom flask. An aqueous HCl solution (10%, 1 mL) was added and the mixture was transferred to a 100-mL Hastelloy B autoclave. 4-Isobutylstyrene 1.28 g, 80 mmol) was added via syringe. The autoclave was purged with CO ($3 \times 500$ psig) and then filled with CO (200 psig). The mixture was agitated at 30° C. for 42 h. GC analysis of an aliquot showed 100% conversion of IBS to ibuprofen. No linear product was observed.

EXAMPLE 2

$PdCl_2$ (29 mg, 0.16 mmol), $CuCl_2$ (50 mg, 0.37 mmol), THF (degassed, 15 mL), and HCl(aq) (10%, 1 mL) Were stirred in a 50-mL round-bottom flask. After io min, a solution of (+)-neomenthyldiphenylphosphine (0.16 g, 0.49 mmol) and 4-isobutylstyrene (1.28 g, 8.0 mmol) in THF (15 mL) was added and the mixture was transferred to a 100-mL Hastelloy B autoclave. The autoclave was purged with CO ($3 \times 500$ psig) and then filled with CO (100 psig). The mixture was agitated at 23° C. for 112 h. GC analysis of an aliquot showed 100% conversion of IBS to ibuprofen. Branched/linear = 100:0.

EXAMPLE 3

$Pd^{+2}/Cu^{+2}$ exchanged montmorillonite KSF (1 g, containing 0.16 mmol Pd) and THF (30 mL) were placed in a 3-neck round-bottom flask. Carbon monoxide (5 mL/min) was bubbled through the mixture for 15 min. HCl(aq) (10%, 0.5 mL) was added and stirred for 5 min. (+)-neomenthyldiphenylphosphine (0.11 g, 0.33 mmol) was added and stirred for another 10 min. 4-Isobutylstyrene (1.28 g, 8.0 mmol) was added and the mixture was transferred to a 100-mL Hastelloy B autoclave. The autoclave was purged with CO ($3 \times 500$ psig) and then filled with CO (300 psig). The mixture was agitated at 100° C. for 92 h. GC analysis of an aliquot showed a 87:13 mixture of ibuprofen and linear product in 43% conversion.

EXAMPLE 4

$PdCl_2$ (29 mg, 0.16 mmol), $CuCl_2$ (70 mg, 0.52 mmol), and $HCl_{(aq)}$ (10%, 1 mL) were stirred in THF (degassed, 15 mL) in a round-bottom flask under CO for 0.5 h. (+)-neomenthyldiphenylphosphine (0.12 g, 0.37 mmol) was added and stirred for an additional 0.5 h. 4-Isobutylstyrene (1.28 g, 8.0 ; mmol) and THF (degassed, 15 mL) were added. The mixture was transferred to a 100-mL Hastelloy B autoclave via syringe. The autoclave was purged with CO ($3 \times 500$ psig) and then filled with CO (30 psig). The mixture was agitated at 100° C. for 2 h. GC analysis of an aliquot showed a 98:2 mixture of ibuprofen and linear product in 100% yield.

EXAMPLE 5

$PdCl_2$ (29 mg, 0.16 mmol), $CuCl_2$ (70 mg, 0.52 mmol), and $HCl_{(aq)}$ (10%, 1 mL) were stirred in THF (degassed, 15 mL) in a round-bottom flask under CO for 1 h. (+)-neomenthyldiphenylphosphine (0.12 g, 0.36 mmol), 4-isobutylstyrene (1.28 g, 8.0 mmol), and THF (degassed, 15 mL) were added and the mixture was transferred to a 100-mL Hastelloy B autoclave via syringe. The autoclave was purged with CO ($3 \times 500$ psig) and then filled with CO (30 psig). The mixture was agitated at 48° C. for 64 h. GC analysis of an aliquot showed only ibuprofen in 100% conversion. No linear product was observed.

EXAMPLE 6

$PdCl_2$ (29 mg, 0.16 mmol), $CuCl_2$ (70 mg, 0.52 mmol), and $HCl_{(aq)}$ (10%, 1 mL) were stirred in THF (degassed, 15 mL) in a round-bottom flask under CO for 0.5 h. (+)-neomenthyldiphenylphosphine (53 mg, 0.16 mmol) was added and stirred for an additional 0.5 h. 4-Isobutylstyrene (1.28 g, 8.0 mmol) and THF (degassed, 15 mL) were added and the mixture was transferred to a 100-mL Hastelloy B autoclave via syringe. The autoclave was purged with CO ($3 \times 500$ psig) and then filled with CO (30 psig). The mixture was agitated at 50° C. for 14 h. GC analysis of an aliquot showed only ibuprofen in 96% conversion. No linear product was detected.

EXAMPLE 7

Carbon monoxide (5 mL/min) was bubbled through THF (30 mL) in a 3-neck, round-bottom flask for 15 min. $PdCl_2$ (29 mg, 0.16 mmol), $CuCl_2$ (70 mg, 0.52 mmol), and $HCl_{(aq)}$ (10%, 1 mL) was added and stirred for 5 min. (+)-neomenthyldiphenylphosphine (0.12 g, 0.37 mmol) was added. After stirring for 5 min, 4-isobutylstyrene (1.28 g, 8.0 mmol) was added and the mixture was kept at 60°–64° C. for 16 h. GC analysis of an aliquot showed an 85:15 mixture of ibuprofen and linear product in 82% conversion.

EXAMPLE 8

Carbon monoxide (5 mL/min) was bubbled through a solution containing $PdCl_2$ (29 mg, 0.16 mmol), $CuCl_2$ (70 mg, 0.52 mmol), an aqueous HCl solution (10%, 1 mL), and THF (degassed, 30 mL) in a 3-neck, round-bottom flask for 1 h. (+)-neomenthyldiphenylphosphine (0.11 g, 0.33 mmol) was added. After 5 min, 4-isobutylstyrene (1.28 g, 8.0 mmol) was added and the mixture was stirred at 40°–45° C. for 18 h. GC analysis of an aliquot showed only ibuprofen in 100 % conversion. No linear product was observed.

EXAMPLE 9

Carbon monoxide (5 mL/min) was bubbled through a solution containing $PdCl_2$ (29 mg, 0.16 mmol), $CuCl_2$ (70 mg, 0.52 mmol), an aqueous HCl solution (10%, 1 mL), and THF (degassed, 30 mL) in a 3-neck, round-bottom flask for 0.5 h. (+)-neomenthyldiphenylphosphine (0.11 g, 0.33 mmol) was added. After 5 min, 4-isobutylstyrene (1.28 g, 8.0 mmol) was added and the mixture was stirred at room temperature (23° C.) for 72 h. GC analyses showed 100% conversion of IBS to ibuprofen. No linear product was formed.

EXAMPLE 10

$PdCl_2$ (18 mg, 0.10 mmol) and (+)-neomenthyldiphenylphosphine (0.10 g, 0.31 mmol) are loaded in an autoclave (Hastelloy B, 100 mL) in a drybox. The reactor was set up in the hood. 4-Isobutylstyrene (1.6 g, 0.010 mol), MeOH (anhydrous, 1.0 g), and MEK (degassed, 19 mL) were added via syringe. The autoclave was purged with CO (3×500 psig) and then pressurized with CO (700 psig). The mixture was agitated at 95°–100° C. for 5 h. GC analysis of an aliquot showed a 97:3 mixture of methyl 2-(4-isobutylphenyl)propionate and methyl 3-(4-isobutylphenyl)propionate in 99% yield.

TABLE 1

Hydrocarboxylation of 4-Isobutylstyrene

| # | Catalyst | Additive | Ligand | Solvt | psig | °C. | hr | Yield | B/L |
|---|---|---|---|---|---|---|---|---|---|
| 1 | $PdCl_2/CuCl_2$ | 10% HCl | 3 eq | THF | 200 | 30 | 42 | 100 | 100/0 |
| 2 | $PdCl_2/CuCl_2$ | 10% HCl | 3 eq | THF | 100 | 23 | 112 | 100 | 100/0 |
| 3 | $PdCl_2/CuCl_2$/ Mont.KSF | 10% HCl | 2 eq | THF | 300 | 100 | 92 | 43 | 87/13 |
| 4 | $PdCl_2/CuCl_2$ | 10% HCl | 2 eq | THF | 30 | 100 | 2 | 100 | 98/2 |
| 5 | $PdCl_2/CuCl_2$ | 10% HCl | 2 eq | THF | 30 | 50 | 64 | 100 | 100/0 |
| 6 | $PdCl_2/CuCl_2$ | 10% HCl | 1 eq | THF | 30 | 50 | 14 | 96 | 100/0 |
| 7 | $PdCl_2/CuCl_2$ | 10% HCl | 2 eq | THF | 0 | 60 | 16 | 82 | 85/15 |
| 8 | $PdCl_2/CuCl_2$ | 10% HCl | 2 eq | THF | 0 | 40 | 18 | 100 | 100/0 |
| 9 | $PdCl_2/CuCl_2$ | 10% HCl | 2 eq | THF | 0 | 23 | 72 | 100 | 100/0 |
| 10 | $PdCl_2$ | MeOH | 3 eq | MEK | 700 | 95 | 5 | 99 | 97/3 |

Ligand = (+)-Neomenthyldiphenylphosphine

TABLE 2

A Comparison of the Rates of the Catalytic Hydrocarboxylation of 4-Isobutylstyrene

| | | % Conversion of Substrate to Product | | | | |
|---|---|---|---|---|---|---|
| Catalyst | Phosphine | 2 h | 4 h | 6 h | 8 h | 10 h |
| $PdCl_2$ | NMDP (3 eq) | 66 | 89 | 97 | 100 | |
| $PdCl_2$ | $Ph_3P$ (3 eq) | 3 | 9 | 11 | 16 | 19 |
| $PdCl_2$ | $CyPh_2P$ (3 eq) | 2 | 5 | 8 | 14 | 18 |
| $PdCl_2$ | $EtPh_2P$ (3 eq) | 0 | 0 | 0 | 0 | 0 |

Conditions:
$P_{co}$ = 500 psig
Temperature = 50° C.
Solvent = THF/$H_2O$ (30:1)
Substrate/catalyst = 50

I claim:

1. A process for preparing an aryl-substituted aliphatic acid or ester thereof having the formula:

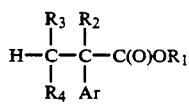

where $R_1$ is hydrogen or alkyl, $R_2$, $R_3$ and $R_4$ are hydrogen, alkyl, cycloalkyl, alkyl-substituted cycloalkyl, aryl either substituted or unsubstituted, alkoxy, alkylthio, heteroaryl either substituted or unsubstituted, alkanoyl, aroyl either substituted or unsubstituted, heteroarylcarbonyl either substituted or unsubstituted, trifluoromethyl or halo and Ar is unsubstituted or substituted aryl which comprises treating a compound of the formula:

where Ar, $R_2$, $R_3$ and $R_4$ are as previously defined and a compound of the formula $R_1OH$ where $R_1$ is as previously defined with carbon monoxide at a pressure of at least about 1 atmosphere and a temperature from about 25° C. to about 200° C. in the absence of oxygen and in the presence of a catalyst that is palladium(0) or the salts of palladium having a valence of 1 or 2 or i) a mixture of said palladium (0) or said salts of palladium and the salts of copper and (ii) a ligand of the formula:

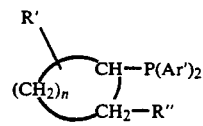

where R' is the same or different than R" and is alkyl or aryl either substituted or unsubstituted and Ar' is phenyl, naphthyl, substituted phenyl or substituted naphthyl and n is an integer from 3 to 6.

2. A process of claim 1 wherein the palladium salt is a palladium(II) salt.

3. A process of claim 2 wherein the palladium salt is palladium(II) chloride.

4. A process of claim 2 wherein the palladium salt is palladium(II) bromide.

5. A process of claim 1 wherein R' and R" are the same or different and are $C_1$ to $C_6$ alkyl, Ar' is phenyl or naphthyl and n is 3 or 4.

6. A process of claim 1 wherein R" is branched $C_3$ to $C_6$ alkyl, R" is methyl or ethyl, Ar' is phenyl and n is 4.

7. A process of claim 6 wherein the ligand is neomenthyldiphenylphosphine.

8. A process of claim 1 wherein the palladium salt is bis(neomenthyldiphenylphosphine)palladium(II) chloride or bromide and the copper salt is copper(I) chloride or copper(II) chloride.

9. A process of claim 1 wherein the amount of palladium metal or palladium salt and copper salt employed is such as to provide about 4–8000 mols of said olefinic compound per mol of palladium metal or palladium salt and copper salt.

10. A process of claim 9 wherein the palladium or palladium salt and copper salt and ligand are employed in amounts such as to provide about 1–20 mols of ligand per mol of palladium or palladium salt and copper salt in the reaction mixture.

11. A process of claim 10 wherein the palladium or palladium salt and copper salt and ligand are employed in amounts such as to provide about 1-12 mols of ligand per mol of palladium or palladium salt and copper salt in the reaction mixture.

12. A process of claim 1 wherein the carbonylation is conducted in the presence of from about 2 to about 24 mols of anhydrous methanol or anhydrous ethanol per mol of said olefinic compound.

13. A process of claim 1 wherein the carbonylation is conducted in the presence of from about 2 to about 24 mol of water per mol of said olefinic compound.

14. A process for preparing ibuprofen or the alkyl esters thereof which comprises carboxylating 4-isobutylstyrene with carbon monoxide in an anhydrous acidic medium containing tetrahydrofuran as a solvent and about 3-24 mols of anhydrous methanol or ethanol per mol of said 4-isobutylstyrene at a temperature in the range of about 25°-120° C. and a carbon monoxide pressure in the range of about 0-1,000 psig in the presence of (a) a mixture of a palladium(II) compound and a copper (II) compound and (b) a ligand of the formula:

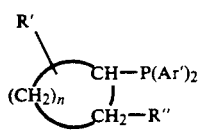

where R' is the same or different than R" and are individually alkyl or aryl, said aryl, either substituted or unsubstituted and Ar' is phenyl, naphthyl, substituted phenyl or substituted naphthyl and n is an integer from 3 to 6, and in the presence of an amount of hydrogen chloride such as to provide an amount up to about 10 mols of hydrogen chloride per mol of 4-isobutylstyrene.

15. A process of claim 14 wherein the palladium(II) compound is palladium(II) chloride the copper (II) compound is copper(II) chloride and the ligand is neomenthyldiphenylphosphine.

16. A process of claim 14 wherein the palladium, the copper, and the ligand are present in amounts such as to provide about 200-2000 mols of said 4-isobutylstyrene per mol of the mixture of palladium and copper compounds and about 1-20 mols of ligand per mol of the mixture of palladium and copper compounds.

17. A process of claim 14 wherein the hydrogen chloride is added as with a concentration from about 10% (by weight) to about 30% (by weight) HCl.

18. A process for preparing ibuprofen or the alkyl esters thereof which comprises carboxylating 4-isobutylstyrene with carbon monoxide in a neutral or acidic medium containing tetrahydrofuran as a solvent and about 2-24 mols of water or an aliphatic alcohol per mol of said isobutylstyrene and no added acid at a temperature in the range of about 25°-100° C. and a carbon monoxide pressure in the range of about 0-1,000 psig, in the copper(II) inorganic salt, and (b) a ligand of the formula:

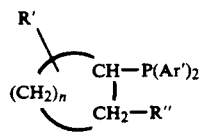

where R' is the same or different than R" and are individually alkyl or aryl, said aryl, either substituted or unsubstituted and Ar' is phenyl, naphthyl, substituted phenyl or substituted naphthyl and n is an integer from 3 to 6, and in the presence of an amount of hydrogen chloride such as to provide an amount up to about 10 mols of hydrogen chloride per mol of 4-isobutylstyrene.

19. A process of claim 18 wherein the palladium (II) salt is palladium(II) chloride and the copper salt is copper(II) chloride and the ligand is neomenthyldiphenylphosphine.

20. A process of claim 18 wherein the palladium and the ligand are present in amounts such as to provide about 200-2000 mols of said 4-isobutylstyrene per mol of the mixture of palladium and copper salts.

21. A process of claim 1 wherein the catalyst is supported on a solvent-insoluble solid materials.

22. A process of claim 21 wherein the solid support is a carbon.

23. A process of claim 21 wherein the solid support is a zeolite.

24. A process of claim 21 wherein the solid support is a clay.

25. A process for preparing ibuprofen ester which comprises carboxylating 4-isobutylstyrene with carbon monoxide in an anhydrous neutral or acidic medium containing about 2-20 mols of a source of alkoxide ions per mol of said olefinic compound at a temperature from about 25° to about 200° C. and a carbon monoxide pressure from about 0 to about 3000 psig in the presence of (a) a palladium(II) compound or (b) a mixture of a palladium(II) compound and a copper(II) compound and a ligand of the formula:

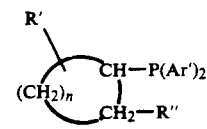

where R' is the same or different than R" and are individually alkyl or aryl, said aryl, either substituted or unsubstituted and Ar' is phenyl, naphthyl, substituted phenyl or substituted naphthyl and n is an integer from 3 to 6, and in the presence of an amount of hydrogen chloride such as to provide an amount up to about 10 mols of hydrogen chloride per mol of 4-isobutylstyrene.

26. A process of claim 25 wherein the source of alkoxide ion is a titanium(IV) alkoxide.

27. A process of claim 25 wherein the source of alkoxide ion is a trialkyl orthoformate.

28. A process of claim 25 wherein the source of alkoxide ion is a alkyl formate.

* * * * *